United States Patent
Castillo

(10) Patent No.: US 9,547,972 B2
(45) Date of Patent: Jan. 17, 2017

(54) METHODS AND SYSTEMS FOR EMERGENCY ALERTS

(71) Applicant: Sal Castillo, San Antonio, TX (US)

(72) Inventor: Sal Castillo, San Antonio, TX (US)

(*) Notice: Subject to any disclaimer, the term of this patent is extended or adjusted under 35 U.S.C. 154(b) by 289 days.

(21) Appl. No.: 14/450,391

(22) Filed: Aug. 4, 2014

(65) Prior Publication Data

US 2015/0161876 A1 Jun. 11, 2015

Related U.S. Application Data

(60) Provisional application No. 61/914,365, filed on Dec. 10, 2013.

(51) Int. Cl.
| | | |
|---|---|---|
| G08B 1/08 | (2006.01) | |
| G08B 21/04 | (2006.01) | |
| G06F 19/00 | (2011.01) | |
| A61B 1/00 | (2006.01) | |
| H04L 1/00 | (2006.01) | |
| A61B 5/00 | (2006.01) | |
| A61B 5/0205 | (2006.01) | |

(52) U.S. Cl.
CPC ....... G08B 21/0453 (2013.01); G06F 19/3418 (2013.01); G08B 21/0446 (2013.01); A61B 1/00 (2013.01); A61B 5/0022 (2013.01); A61B 5/02055 (2013.01); A61B 5/6802 (2013.01); A61B 5/746 (2013.01); H04L 1/00 (2013.01)

(58) Field of Classification Search
CPC .................................... A61B 1/00; H04L 1/00
See application file for complete search history.

(56) References Cited

U.S. PATENT DOCUMENTS

| | | | | |
|---|---|---|---|---|
| 2002/0054174 A1* | 5/2002 | Abbott | ............... | G06F 1/163 715/863 |
| 2005/0091368 A1* | 4/2005 | Ozburn | ............... | G06Q 10/10 709/224 |
| 2013/0173297 A1* | 7/2013 | Hyde | ............... | G06Q 50/24 705/3 |
| 2014/0266160 A1* | 9/2014 | Coza | ............... | G01B 7/003 324/207.11 |

* cited by examiner

Primary Examiner — Shirley Lu
(74) Attorney, Agent, or Firm — Pierson IP, PLLC

(57) ABSTRACT

Embodiments disclosed herein provide systems and methods for biometric sensors being embedded in a wearable computing device. The biometric sensors may determine a user's biometric data, and the determined biometric data may be transmitted to a biometric server over a network. In response to receiving the biometric data, the biometric server may parse the received biometric data to determine if an emergency alert signal should be transmitted to third parties.

7 Claims, 4 Drawing Sheets

METHODS AND SYSTEMS FOR EMERGENCY ALERTS

CROSS-REFERENCE TO RELATED APPLICATIONS

This application claims a benefit of priority under 35 U.S.C. §119 to Provisional Application No. 61/914,365 filed on Dec. 10, 2013, which is fully incorporated herein by reference in its entirety.

BACKGROUND INFORMATION

Field of the Disclosure

Examples of the present disclosure relate to techniques for communicating emergency alerts. More particularly, embodiments are related to wearable technology comprising sensors that may trigger the emergency alerts.

Background

Conventional devices capable of transmitting "personal assistance needed" or emergency alert signals to remote friends, relatives, caregivers, and emergency personnel ("third parties") are generally known. However, these devices require an active step by the wearer of the device to perform actions to communicate an emergency alert signal notifying a third party of the existence of a medical, personal, or other emergency. For example, certain conventional devices effectively function as wearable, easy-to-use transmitters that communicate the emergency alert signal in response to the wearer of the device pressing a button or some other affirmative action to trigger transmitting the alert signal. Persons with potential need for such devices include older adults, individuals living alone, persons with disabilities or chronic diseases, and individuals working in high risk occupations. Yet, these people may not be able to perform the affirmative action to transmit the alert signal for various reasons.

Hospitals and other medical facilities use conventional sensors to monitor the status of patients and the facilities. These conventional sensors may detect smoke, fire, pathogens, heart rates, breathing rates, EEG, blood oxygen levels, etc. These conventional sensors are hardwired within a closed circuit to give off an audible alarm or flashing light that alert third parties of an emergency situation. However, these conventional sensors cannot monitor beyond confined area due to the restriction of requiring a hard wired connection. Current monitors also restrict wearer's movement and are easy to disconnect.

Accordingly, needs exist for more efficient and effective emergency alert systems that may automatically transmit an emergency alert signal to designated responders.

SUMMARY

Embodiments disclosed herein provide systems and methods for a wearable computing device with a wearable embedded biometric sensor device. The biometric sensors may determine a user's biometric data and location. The wearable computing device may transmit the determined biometric data to a biometric server over a network. In response to receiving the biometric data, the biometric server may parse the received biometric data to determine if the wearer of the wearable device is in an emergency situation, and transmit an emergency alert signal to third parties. In embodiments, an emergency alert signal may be triggered by the wearer's physiological changes measured by the wearable device embedded with biometric sensors.

In embodiments, the system includes configurable software that allows a user to define thresholds for various embedded sensors, or the system may include default thresholds or settings that may not be adjusted. Embodiments may also be configured to automatically interpret the data from the biometric sensors as a safety or health risk, monitor health and safety risks with nearly unrestricted mobility, and automatically transmit an alert notification to interested or desired third parties to allow immediate and appropriate response.

In embodiments, the emergency alert signal may be transmitted if the biometric server determines that the biometric data is outside of the normal parameters set by the wearer of the wearable device or the biometric server determines a rapid change in the biometric data, which may indicate the possibility of an emergency situation.

In embodiments, the wearable device may be a bracelet, necklace, ring, or article clothing, which may be based on what is most desirable for the individual or commercial need.

In embodiments, the wearable device may measure biometric data from a plurality of sensors embedded within or on the wearable device. Based on a combination of the plurality of sensors measurements, the wearable device or biometric server may determine if there is a possible threat to the wearer's safety or health. Responsive to determining there is a possible threat to the wearer's safety or health, the wearable device or biometric server may transmit the emergency alert signal automatically without requiring the wearer to perform any actions or commands to transmit the emergency alert signal.

Embodiments may be customized to meet a wearer's personal needs or the needs of a monitoring entity associated with the wearer. Embodiments may be customized by the user or the monitoring entity by performing actions to set thresholds corresponding to the biometric sensors indicating a possible threat to the user's safety or health. Embodiments may be further customized by the wearer performing actions to determine what biometric sensors may be used to determine a possible threat to the wearer's safety or health.

In embodiments, the following biometric sensors may be embedded within the wearable device:
  Multiple axis accelerometers,
  Multiple axis gyroscopes
  Pulse oximeter heart monitor,
  Acoustical heart monitor,
  Galvanic skin monitor,
  Near Field Communication (NFC) Sensors for Alcohol and Drugs,
  Toxic environment gas monitor,
  Cardiac rhythm authentication.

In embodiments, the emergency alert signal may be configured to be transmitted via Bluetooth, NFC, or any other wireless protocol. Responsive to transmitting the emergency alert signal, the wearable device may initiate a speaker, camera, microphone, light, etc. disposed on either the user's wearable device or a separate synchronized wireless standalone device.

Embodiments may be configured to automatically transmit the emergency alert signal to onsite authorities responsive to dramatic physiological changes in a wearer, wherein the threat of violence or an emergency situation is possible. Accordingly, a health related emergency associated with the wearer of the wearable device may be quickly and effectively handled.

Embodiment may also include encryption, ghost location option, and configurable wireless wearable devices that make simple video surveillance a thing of the past. As soon as a threat or an emergency situation is detected by a wearable computing device.

In embodiments, officials associated with the third party computing device can respond to the emergency or threat by first validating the threat or emergency, and if necessary respond to the threat or emergency once the threat of emergency has been confirmed.

These, and other, aspects of the invention will be better appreciated and understood when considered in conjunction with the following description and the accompanying drawings. The following description, while indicating various embodiments of the invention and numerous specific details thereof, is given by way of illustration and not of limitation. Many substitutions, modifications, additions or rearrangements may be made within the scope of the invention, and the invention includes all such substitutions, modifications, additions or rearrangements.

BRIEF DESCRIPTION OF THE DRAWINGS

Non-limiting and non-exhaustive embodiments of the present invention are described with reference to the following figures, wherein like reference numerals refer to like parts throughout the various views unless otherwise specified.

Figure 1:
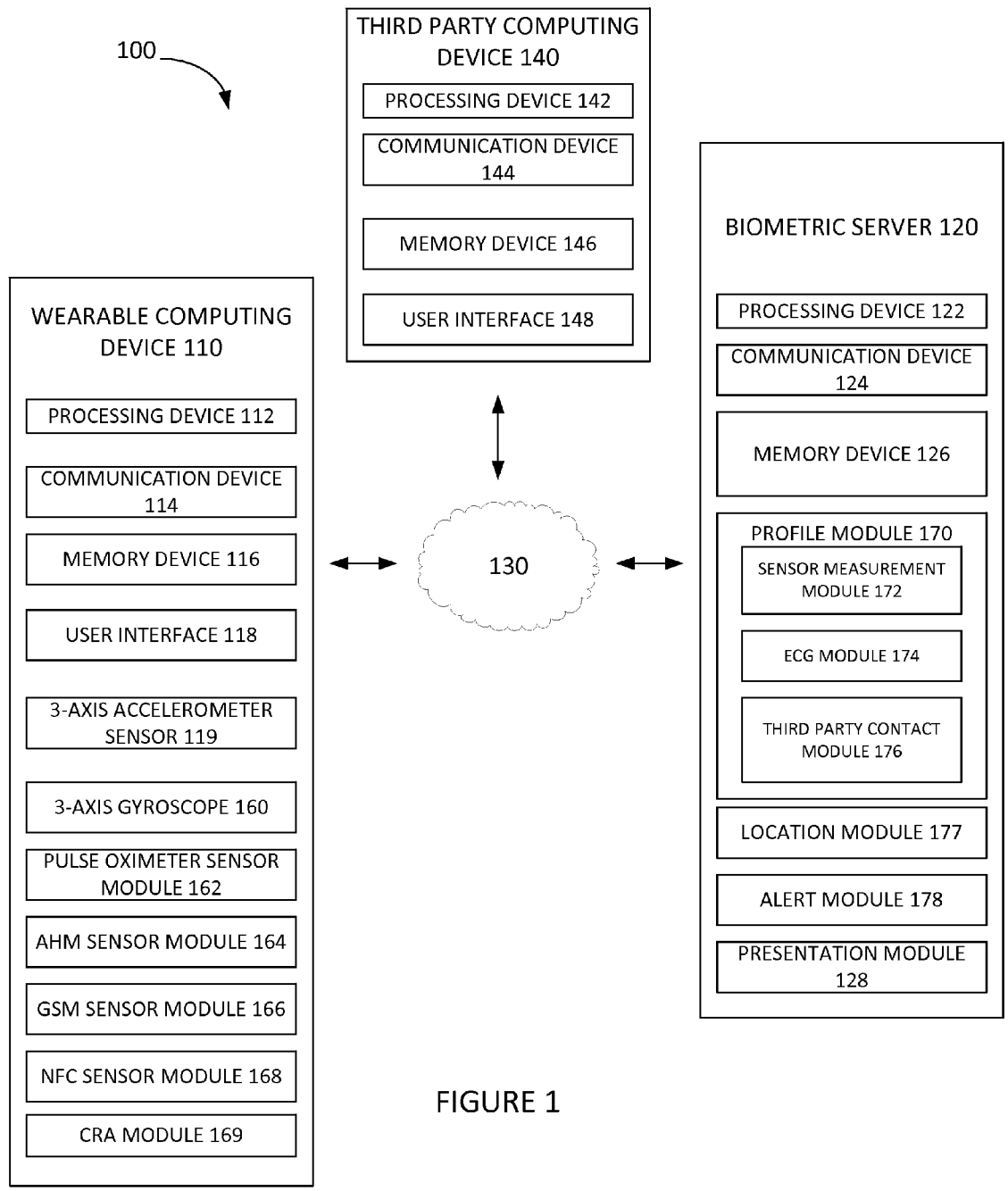
FIG. 1 depicts one embodiment of a topology for automatically transmitting an emergency alert signal based on biometric data measured from sensors embedded within a wearable computing device.

Corresponding reference characters indicate corresponding components throughout the several views of the drawings. Skilled artisans will appreciate that elements in the figures are illustrated for simplicity and clarity and have not necessarily been drawn to scale. For example, the dimensions of some of the elements in the figures may be exaggerated relative to other elements to help to improve understanding of various embodiments of the present disclosure. Also, common but well-understood elements that are useful or necessary in a commercially feasible embodiment are often not depicted in order to facilitate a less obstructed view of these various embodiments of the present disclosure.

DETAILED DESCRIPTION

In the following description, numerous specific details are set forth in order to provide a thorough understanding of the present invention. It will be apparent, however, to one having ordinary skill in the art that the specific detail need not be employed to practice the present invention. In other instances, well-known materials or methods have not been described in detail in order to avoid obscuring the present invention.

Turning now to FIG. 1, FIG. 1 depicts one topology 100 for automatically transmitting an emergency alert signal based on biometric data measured from sensors embedded within a wearable computing device 110. Topology 100 may include wearable computing device 110, biometric server 120 and a third party computing device 140. The elements depicted in topology 100 may be communicatively coupled to each other over network 130.

Network 130 may be a wired or wireless network such as the Internet, an intranet, a LAN, a WAN, Bluetooth network, NFC network, a cellular network, or another type of network. It will be understood that network 130 may be a combination of multiple different kinds of wired or wireless networks, which may operate over different protocols.

Wearable computing device 110 may be a smart phone, tablet computer, laptop computer, wearable computer, ring computer, necklace computer, smart-watch, personal data assistant, computer embedded within an article of clothing, or any other type of mobile device with a hardware processor that is configured to process instructions, connect to network 130, connect to one or more portions of network 130, and communicate data over network 130 to other computing devices. Wearable computing device 110 may include processing device 112, communication device 114, a memory device 116, a user interface 118, 3-axis accelerometer sensors 119, 3-axis gyroscope 160, pulse oximeter sensor 162, acoustical heart monitor sensor module 164, galvanic skin monitor sensor 166, NFC sensor for alcohol and/or drugs ("NFC sensor module") 168, cardiac rhythm authentication module 169.

Processing device 112 can include memory, e.g., read only memory (ROM) and random access memory (RAM), storing processor-executable instructions and one or more processors that execute the processor-executable instructions. In embodiments where processing device 112 includes two or more processors, the processors may operate in a parallel or a distributed manner. Processing device 112 may execute an operating system of wearable computing device 110 or software associated with other elements of wearable computing device 110.

Communication device 114 may be a hardware device that allows wearable computing device 110 to communicate with another device, e.g., biometric server 120 over network 130. Communication device 114 may include one or more wireless transceivers for performing wireless communication and/or one or more communication ports for performing wired communication. Communication device 114 may be configured to communicate data over network 130 according to a plurality of different protocols and/or standards, such as Wi-Fi, 3G, 4G, Bluetooth, NFC, etc.

Memory device 116 may be a hardware device configured to store data generated or received by wearable computing device 110. Memory device 116 may include, but is not limited to a hard disc drive, an optical disc drive, and/or a flash memory drive. Memory device 116 may be configured to store data associated with a wearer's biometric data, data determined by modules or sensors disposed on or embedded within wearable computing device 110, thresholds corresponding to at least one of the sensors and modules: 160, 162, 164, 166, 168, 169 associated with emergency situations or any other information transmitted to or received from biometric server 110.

User interface 118 may be a hardware device configured to allow a user to interact with wearable computing device 110 or biometric server 120 over network 130. While one user interface is shown, the term "user interface" may include, but is not limited to being, a touch screen, a physical keyboard, a mouse, a camera, a video camera, a microphone, and/or a speaker. Utilizing user interface 118, the wearer of wearable computing device 110 may customize biometric sensor thresholds that may trigger an emergency alert signal being transmitted, perform commands to enter contact information where the emergency alert signal should be transmitted, enter data associated with a wearer's profile, which may include medical information of the wearer, a height of the wearer, a weight of the wearer, contact information of the wearer, blood type of the wearer, allergies of the wearer, a home address of the wearer, etc. One skilled in the art will appreciate that user interface 118 may be a port or interface, such as a USB port or a wireless communications port, configured to allow wearable computing device 110 to communicate with a conventional computing device. When wearable computing device 110 is coupled to a conventional computing device, user interface 118 may include the interfaces of the conventional computing device, such as the conventional computing device's keyboard, mouse, touchscreen, display, etc.

3-Axis accelerometer sensors 119 may be a hardware computing device configured to determine acceleration associated with the weight experienced by wearable computing device 110 in a frame of reference. Furthermore, axis accelerometer sensors 119 may be configured to determine measurements associated with the acceleration of wearable computing device 110, vibrations of wearable computing device 110, a distance or speed travelled by wearable computing device 110, etc. In embodiments, axis accelerometer sensors 119 may determine measurements that are quantified in meters per second square or G-force. In embodiments, 3-axis accelerometers sensors 119 may also be configured to determine a wearer's orientation such as prone, supine, and degree of tilt, and may also be configured to determine crash strength g-forces for automatic collision notification.

3-axis gyroscope module 160 may be a hardware computing device configured to determine a wearer's orientation with respect to angular momentum. For example, 3-axis gyroscope module 160 may be configured to determine rotational forces experienced by a wearer of wearable computing device 110 that may result in injury when a wearer experiences increased force resulting from possible spinning or rotation from a fall, crash, or physical altercation.

Pulse oximeter module 162 may be a hardware computing device configured to determine a wearer's of wearable computing device 110 oxygen saturation levels. In embodiments, pulse oximeter module 162 may measure the percentage of blood that is loaded with oxygen for the wearer of wearable computing device 110, and more specifically what percentage of the wearer's protein in the blood that carries oxygen is loaded. A normal range of a wearer's blood that is loaded with oxygen may be between ninety-five to ninety-nine percent. In embodiments, pulse oximeter module 162 may be configured to measure the wearer's oxygen saturation levels in saturation of peripheral oxygen ($SpO_2$).

Acoustical heart monitor module 164 may be a hardware computing device configured to determine acoustic data associated with the heart of the wearer of wearable computing device 110. Acoustical heart monitor 164 may use a Doppler effect to transmitting 2 MHz-5 MHz probes to determine the wearer's heart rate. In embodiments, acoustical heart monitor 164 may acquire, record, and analyze the acoustic signals of the heart of the wearer wearing wearable computing device 110. Responsive to analyzing the acoustic signals of the wearer's heart, acoustical heart module 164 may convert the received acoustic signals into electrical heart data. In further embodiments, acoustical heart monitor module 164 may be configured to determine the heart rate of a wearer of wearable computing device 110 in addition to pulse oximeter module 162. Accordingly, heart rate monitor module 164 may be a redundant heart rate sensor.

Galvanic skin monitor module 166 may be a hardware computing device configured to determine an electrical conductance of the skin of the wearer wearing wearable computing device 110. The electrical conductance of the skin of the wearer may vary based on the moisture level of the wearer wearing wearable computing device 110. In embodiments, the electrical conductance of the skin of the wearer wearing wearable computing device 110 may be an indication of psychological or physiological arousal of the wearer. Galvanic skin monitor module 166 may determine the electrical conductance of the wearer's skin in Siemens (S).

NFC sensor module 168 may be a hardware computing device configured to measure the blood alcohol level (BAC) in a body of a wearer wearing wearable computing device 110. NFC sensor module 168 may be configured to detect ethanol in the air. An electrical current may be produced by NFC sensor module 168 in response to the oxidation of the ethanol in wearer's perspiration.

Cardiac rhythm authentication module 169 may be a hardware computing device configured to authenticate the wearer of wearable computing device 110 based on the unique cardiac rhythm of the heart of the wearing wearable computing device 110. In embodiments, cardiac rhythm authentication module 169 may receive information associated with the wearer's heart over a period of time to measure the rate and regularity of the user's heartbeat to determine the user's electrocardiogram (ECG). Because each wearer may have a different ECG, cardiac rhythm authentication module 169 may be configured to store the wearer's ECG within memory device 116, and compare the stored ECG within memory device 116 with the user wearing wearable computing device 110 ECG. If the wearer's stored ECG within memory device 116 matches the ECG of the user wearing wearable computing device 110, cardiac rhythm authentication module 170 may be configured to determine that the wearer is authenticated to wear wearable computing device 110. Furthermore, cardiac rhythm authentication module 169 may include a FIPS certified encryption and ghost location where wireless transmission intercepts by unauthorized entities could prevent, limit, or reduce compromising the safety of a user wearing wearable computing device 110. In embodiments, cardiac rhythm authentication module 169 may be configured to ensure the wearer of the wearable computing device 110 is who they say they are. Accordingly, cardiac rhythm authentication module 169 may limit, reduce, or eliminate an unauthorized user from wearing wearable computing device 110 based on the ECG of the wearer. Therefore wearable computing device 110 could not be used by anyone else if the wearable computing device 110 is programmed to only allow an authenticated user to transmit data (e.g., data from modules 119, 160, 162, 164, 166, or 168) from wearable computing device 110.

One skilled in the art will appreciate that wearable computing device 110 may include further sensors, modules, monitors, etc. The sensors and monitors may be configured to measure biometric data and/or environmental data associated with a wearer of wearable computing device.

Biometric server 120 may be a computing device, such as a general hardware platform server configured to support mobile applications, software, and the like executed on wearable computing device 110 and/or third party computing device 140. Biometric server 120 may include physical computing devices residing at a particular location or may be deployed in a cloud computing network environment. In this description, "cloud computing" may be defined as a model for enabling ubiquitous, convenient, on-demand network access to a shared pool of configurable computing resources (e.g., networks, servers, storage, applications, and services) that can be rapidly provisioned via virtualization and released with minimal management effort or service provider interaction, and then scaled accordingly. A cloud model can be composed of various characteristics (e.g., on-demand self-service, broad network access, resource pooling, rapid elasticity, measured service, etc.), service models (e.g., Software as a Service ("SaaS"), Platform as a Service ("PaaS"), Infrastructure as a Service ("IaaS"), and deployment models (e.g., private cloud, community cloud, public cloud, hybrid cloud, etc.).

Biometric server 120 may include any combination of one or more computer-usable or computer-readable media. For example, biometric server 120 may include a computer-readable medium including one or more of a portable computer diskette, a hard disk, a random access memory (RAM) device, a read-only memory (ROM) device, an erasable programmable read-only memory (EPROM or Flash memory) device, a portable compact disc read-only memory (CDROM), an optical storage device, and a magnetic storage device.

In embodiments, biometric server 120 may include a processing device 122, a communication device 124, a memory device 126, a profile module 170, a location module 177, an alert module 178, and a presentation module 128.

Processing device 122 may include memory, e.g., read only memory (ROM) and random access memory (RAM), storing processor-executable instructions and one or more processors that execute the processor-executable instructions. In embodiments where processing device 122 includes two or more processors, the processors may operate in a parallel or distributed manner. Processing device 122 may execute an operating system of biometric server 120 or software associated with other elements of biometric server 120.

Communication device 124 may be a device that allows biometric server 120 to communicate with another device over network 130. Communication device 124 may include one or more wireless transceivers for performing wireless communication and/or one or more communication ports for performing wired communication.

Memory device 126 may be a device that stores data generated or received by biometric server 120. Memory device 126 may include, but is not limited to a hard disc drive, an optical disc drive, and/or a flash memory drive. In embodiments, memory device 126 may be configured to store information received from wearable computing device 110 and/or third party computing device 140. The information stored within memory device 126 may be accessed by processing device 122, communication device 124, and/or modules 170, 172, 174, 176, 177, 178, 179, and 128. In embodiments, memory device 126 may include a database with an entry associated with the wearer of wearable computing device 110. The entry for the wearer within memory device may be configured to store user information associated with the wearer of wearable computing device 110 and/or alert information associated when an emergency alert signal should be transmitted for alert module 178. For example, the database entry may include baseline values associated with the wearer's biometric data and/or threshold values associated with when an emergency alert signal should be transmitted, wherein the threshold values may be dynamically changed by the user or are set default values.

Profile module 170 may be configured to allow a wearer of a wearable computing device server 110 to generate and create a profile that includes information associated with the wearer. The wearer's profile may be stored in memory device 126, wearable computing device 110, biometric server 120, and/or other storage locations accessible over network 130. The wearer's profile may include, for example, information identifying the wearer (e.g., the wearer's name, a username or handle, a number, an identifier, and/or other identifying information), security login information (e.g., a login code or password), pictures of the wearer, biographic information of the wearer (e.g., the wearer's height, weight, etc., the wearer's contact information (e.g., a phone number of the wearer), and/or the wearer's home address or work address. In embodiments, profile module 170 may also include sensor measurement module 172, ECG module 174, and third party contact module 176.

Sensor measurement module 172 may be a hardware device configured to receive sensor data from modules 119, 160, 162, 164, 166, 168, and 169 disposed within wearable computing device 110. The received data information may be the information determined by a corresponding sensor or module on wearable computing device 110. For example, the received sensor data determined by axis accelerometers module 119 may be data corresponding to meters per second that wearable computing device 110 is moving. Responsive to receiving the sensor data, sensor measurement module 172 may store the sensor information along with a time-stamp associated with a time that the sensor data is received, wherein the sensor information and the time stamp may be stored within the entry for the wearer of wearable computing device 110 within memory device 126.

ECG module 174 may be configured to receive ECG information associated with the wearer of wearable computing device 110 ECG. ECG module 174 may be configured to store the ECG information of the wearer within the entry for the wearer within memory device 126. ECG module 174 may also be configured to compare a received ECG from wearable computing device 110 with the ECG information stored within wearers' entries within memory device 126. Upon ECG matching the received ECG with an ECG within a wearer's entry within memory device 126, ECG module 174 may determine which user is wearing wearable computing device 110.

Third party contact module 176 may be configured to receive contact information associated with third parties. The contact information may be a phone number or email address of third parties (e.g., a friend, family member, neighbor, doctor, 911, etc.) may be stored within the entry for a wearer. In embodiments, the contact information may be stored in the entry for the wearer within memory device 126 along with an identifier for a type of an emergency situation, such that a first third party may be contacted in response to alert module 178 determining that a first type of emergency situation has occurred and a second third party may be contacted in response to alert module 178 determining that a second type of emergency situation has occurred.

Location module 177 may be a hardware device configured to determine the location of wearable computing device 110 and/or third party computing device 140. Location module 177 may be configured to receive location information from wearable computing device 110 and/or third party computing device 140, wherein the location information may be associated with and represented in geographic coordinates, Cartesian coordinates, and/or a name of a location. In embodiments, location module 177 may receive location data such as real-time locating system signals (RTLS), Wi-Fi signals, GPS, Bluetooth, short range radio signals, etc. from wearable computing device 110 and/or third party computing device 140. In embodiments, location module 177 may be configured to determine the location of wearable computing device 110 responsive to alert module 178 determining an emergency situation is occurring or alert module 178 transmitting an emergency alert signal. Responsive to determine the location of wearable computing device 110, location module 177 may be configured to determine a closest third party computing device 140 to wearable computing device 110 based on the received location information of wearable computing device 110 and location information associated with third party computing device 140 stored within memory device 126.

Alert module 178 may be a hardware device configured to determine if an emergency situation has occurred responsive to receiving sensor data from wearable computing device 110 as determined by modules 119, 160, 162, 164, 166, 168, 170. Alert module 178 may set threshold values or change thresholds associated with received data from modules 119, 160, 162, 164, 166, 168, or 170. The threshold ranges or change threshold may be associated with if an emergency situation has occurred or if a quality check is desired to determine the cause of the emergency situation. The threshold ranges may set values associated with the wearer's biometric data, and the change thresholds may be associated with a change in values over a period of time. In embodiments, the threshold ranges may include a lower threshold and/or an upper threshold.

In embodiments, if the received sensor data from wearable computing device 110 is outside of the threshold ranges or 170 and/or the received sensor data indicates a change in sensor data over a period time that is greater than a change threshold associated with the corresponding module, alert module 178 may determine different types of emergency situations have occurred. When alert module 178 determines an emergency situation has occurred, alert module 178 may transmit an emergency alert signal to a third party computing device 140.

In further embodiments, alert module 178 may determine that an emergency threshold has occurred responsive to the received data from wearable computing device 110 being outside a corresponding threshold range over a period of time, wherein the period of time is any desired length of time. In embodiments, the transmitted emergency alert signal may be a phone call, text, e-mail, social media message, pre-recorded voice mail message, etc.

The following are non-limiting embodiments of alert module 178 determining a type of emergency situation has occurred for a user's individual safety.

In a first embodiment, alert module 178 may determine that an emergency situation that is a possible threat to the health or safety of the wearer wearing wearable computing device's 110 based on a rapid change to the physiology of the wearer of wearable computing device's 110. The body's natural response to an event when the wearer of wearable computing device's 110 is faced with danger may be the immediate release of the hormone adrenalin. This hormone activates a "fight or flight" response, and physiological changes to the wearer of wearable computing device 110 may occur over a few seconds, which may be detected by modules 119, 160, 162, 164, 166, 168, 169. For example, in an emergency situation, the heart of the wearer wearing wearable computing device 110 may have an increase in heart rate and their respiration rate may also increase. Responsive to alert module 178 determining that the heart rate of the wearer wearing wearable computing device 110 is increased or decreased based on data received from pulse oximeter 162 to levels greater than a heart rate change threshold and/or outside of a threshold range, alert module 178 may begin a quality check for a possible cause of the increase or decrease of the wearer's heart rate. In embodiments, after received data indicates that the heart rate of the wearer is greater than a change threshold, it may be determined if the heart rate of the wearer is outside of a threshold range for a prolonged period of time. Accordingly, utilizing both the change threshold and threshold range it may be determined if the wearer is merely startled or in a prolonged emergency state.

In embodiments, if the wearer's heart rate and blood oxygen levels of the user wearing wearable computing device 110 have continued to increase or decrease over a period of time, which may be any desired length of time, then alert module 178 may determine the wearer's skin temperature based on data received from galvanic skin monitor 166. If the wearer's skin temperature is increased past a change threshold associated with the wearer's skin temperature, alert module 178 may determine the wearer's movement based on data received from axis accelerometer 119. If alert module 178 determines that the wearer's movement is greater than a change threshold associated with the wearer's movement, alert module 178 may determine that the wearer is in an emergency situation, where the wearer is incapacitated or struggling.

In further embodiments, galvanic skin module 166 may be configured to detect heat exhaustion and life threatening fevers or heat stroke of a wearer of wearable computing device 110 if the change threshold associated with the wearer's skin temperature is above a second change threshold, which may be greater than a first change threshold. Furthermore, responsive to determining a wearer's blood oxygen saturation and heart rate have changed to levels greater than corresponding change thresholds, alert module 178 may determine that the wearer is experiencing shock. In further embodiments, alert module 178 may be configured to determine if the wearer has no pulse, no blood oxygen, and/or no movement.

Responsive to alert module 178 determining that the wearer is incapacitated or struggling based on the received biometric data, change thresholds, and/or threshold ranges, alert module 178 may transmit an emergency alert signal to at least one third party, wherein the third party may be determined based on type of emergency situation. In further embodiments, alert module 178 may delay sending the alert signal for a period of time, wherein the wearer may perform commands on user interface 118 wearable computing device 110 to disable the transmission of the emergency alert signal. As such, the delay may limit the number of emergency alert signals transmitted when the wearer is accidently frightened. In embodiments, the period of time associated with the delay may be fixed, and/or may be dynamically adjusted by a wearer.

In a second embodiment, a wearer of wearable computing device 110 may become incapacitated by an injury, such as a fall or wreck. Responsive to the fall or wreck, alert module 178 may receive data from axis accelerometer 119 and gyroscope module 160 indicating a sudden change in the body position of the wearer based on a change in G-Force being greater than a change threshold (e.g., 1 G-Force) associated with axis accelerometer 119 and gyroscope 160. Responsive to the data from axis accelerometer 119 being greater than the change threshold for the axis accelerometer 119, alert module 178 may parse the data associated with modules 119, 162, 164, 166, 168, and/or 169. For example, alert module 178 may determine if data received from pulse oximeter module 162 indicates a change in blood oxygen level greater than a change threshold associated with pulse oximeter module 162, this may indicate that the wearer of wearable computing device 110 fainted before the user fell. Therefore, if the change in blood oxygen level greater than the change threshold associated with pulse oximeter module 162 occurred within a time period (e.g. one minute) of the change in the G-Force of the wearer being greater than the change threshold associated with axis accelerometer 119, then alert module 178 may determine that the wearer of wearable computing device 110 has fallen down and transmit an emergency alert signal to the third parties associated with a fall of the wearer. Accordingly, different types of emergency situations may be based on data associated with different modules, and threshold associated with the corresponding modules.

In further embodiments, if the data received from axis accelerometer 119 is greater than a second change threshold (e.g., 2-G) associated with axis accelerometer 119, then an alert signal may be transmitted regardless of the wearer's change in blood oxygen level. This is because a force of more than 2G could result in a greater injury than a smaller force. However, should a wearer's heart rate decline and blood oxygen level subsequently decline subsequent to an axis accelerometer and/or gyroscope change threshold be exceeded, alert module 178 may determine that a wearer of wearable computing device 110 has experienced a wound that is now resulting in internal or external loss of blood.

In a third embodiment, a wearer of wearable computing device 110 may not notice a small increase in their body temperature. However, this could be a sign of infection or heat stroke. Alert module 178 may be configured to determine that received data from galvanic skin monitor 166 indicates that the body temperature of the wearer wearing wearable computing device 110 is greater than a change threshold associated with galvanic skin monitor 166. Responsive to alert module 178 determining that the body temperature of the wearer wearing wearable computing device 110 is greater than the body temperature change threshold, alert module 178 may determine if the wearer's heart rate has increased based on data received from pulse oximeter 162 to levels greater than a threshold range. If the data received from pulse oximeter 162 indicates that the wearer's heart rate has changed past a heart rate threshold range and the data received from galvanic skin monitor 166 indicates that wearer's body temperature has changed past a body temperature change threshold, alert module 178 may transmit an emergency alert signal to at least one third party associated with this type of emergency situation.

The following are non-limiting embodiments of alert module 178 determining a type of emergency situation has occurred for a commercial wearer wearing wearable computing device 110. In embodiments, biometric server 120 may monitor a wearer to protect not only themselves, but also to monitor the safety and health of others if an emergency situation occurs. Accordingly, embodiments may be customizable by the wearer or an administrator of biometric server 120 to disable modules 119, 160, 162, 164, 166, 168, 169 from transmitting data to biometric server 120. Therefore, unwanted information may not be transmitted if it is not required or desired to monitor a specific type of emergency or a wearer of wearable computing device 110 may not be able to modify the transmitted data. Therefore, administrators know that the transmitted data has not been adjusted by the wearer, and the administrators may be required to only monitor specific data determined by the modules of wearable computing device 110.

In embodiments, threshold ranges associated with data from modules 119, 160, 162, 164, 166, or 168 may not be important or defined by a wearer of wearable computing device 110. For example, in one embodiment a threshold range associated with the blood oxygen levels of a user may not be defined. This may prevent accidental or deliberate attempts to mask the readings. While certain populations may have lower than normal blood oxygen levels and still be considered normal, in embodiments, third parties such as law enforcement and military may have emergency alert signals automatically transmitted to their computing devices immediately when data received from pulse oximeter indicates that the blood oxygen levels of a wearer wearing wearable computing device 110 dropped even slightly. This may ensure that the wearer of wearable computing device 110 is not being poisoned, slowly suffocating, or just shallow breathing.

In a further embodiment, axis accelerometers 119 may be configured to operate in tandem with axis gyroscope module 160, wherein axis accelerometer 119 and axis gyroscope module 160 may be configured to identify certain gestures. Responsive to the axis accelerometers 119 determining the certain gestures, wearable computing device 110 may transmit a signal to vibrate a haptic device disposed on the third party computing device 140, wherein the signal may cause the haptic device to vibrate at different lengths of times of intervals based on the determined gesture. For instance, axis accelerometers 119 and/or axis gyroscope module 160 may be configured to determine the wearer of wearable computing device 110 made a circular hand gesture above the wearer's head. Responsive to determining that that wearer of wearable computing device 110 made the circular hand gesture above the wearer's head, wearable computing device 110 may transmit a signal to cause third party computing device 110 to vibrate twice. In embodiments, the determined gestures may have a specific meaning which can be interpreted based on the length of time of the vibrations, the intervals of vibration, force of the vibrations, and/or number of vibrations. For example, two short vibrations on third party computing device 140 may be interpreted as "stand down."

In further embodiments, axis accelerometers 119 may be configured to assist a tactical response. Biometric server 120 may be configured to receive location information determining the location of wearable computing device 110. Based on the location of wearable computing device 110 and the speed wearable computing device 110 determined by axis accelerometers 119, an estimated time of arrival to a second location may be determined. If a situation arises where audible communication may be undesired, biometric server 120 may be configured to transmit a Morse code type signal to third party computing device 140, wherein the meaning of the Morse code type signal may be interpreted based on the length of time of the vibrations, the intervals of vibration, the strength of the vibration, and/or number of vibrations.

In further embodiments, biometric server 120 may be configured to monitor vital statistics of a wearer wearing wearable computing device 110, wherein the wearer may be involved in the safe transport of humans or materials. A wearer of wearable computing device 110 involved in transporting goods, may not only need to protect themselves, but having biometric server 120 transmit an emergency alert signal to third parties immediately without having to perform actions to warn or alert the third parties of the emergency situation may make handling the emergency situation easier. To this end, by biometric server 120 being an instant alert system, a person committing a criminal act may be less likely to succeed or possibly deterred if biometric server 120 cannot be compromised by threats. This may be because as soon as biometric server 120 detects a physiologic change to the wearer of wearable computing device 110 that is greater than a change threshold associated with a corresponding sensor data, biometric server 120 may transmit an emergency alert signal to a third party computing device 140. Furthermore, if biometric server 120 determines a sudden and unexpected change in the health or physiology based on data received from modules 119, 160, 162, 164, 166, or 168 being greater than a change threshold associated with the corresponding module, the wearer with the changed health or physiology may pose a threat to the passengers. Embodiments include law enforcement, military, and high security occupations in government (TSA, HSA, FBI, CIA, etc.). Transportation of hazardous materials, airline pilots, bus drivers, train engineers, all require assurance of utmost levels of focus, concentration, and attention. Embodiments include monitoring the vital signs as well as any possible impairment due to drugs and alcohol. Therefore, by biometric server 120 determining the received data is greater than a corresponding change threshold and transmitting an alert signal to a desired third party computing device 140, the opportunity to mitigate damage or prevent injury may be increased.

Embodiments may consider response time to transmit the alert signal to be a paramount feature and entities will be able to customize what actions are caused by an alert signal to meet the needs of the industry. Further embodiments may be used in educational, governmental, and commercial environments to assist first responders to an emergency.

Embodiments may utilize cameras positioned disposed on or within buildings configured to receive audio or video data, such that the first responders may see in real time what is happening at the building. Biometric server 120 may be communicatively coupled to sirens and/or flashing lights disposed on or within the building, and biometric server 120 may be configured to transmit a signal to initiate the sirens and/or flashing lights to warn others of a dangerous situation in order to reduce collateral damage. Additionally, financial institutions such as banks, credit unions, currency exchanges, gold and silver dealers, armored car services, etc. can have all staff outfitted with wearable computing device 110 with customizable settings to ensure efficiency and effectiveness.

Presentation module 128 may be configured to transmit information configured to be displayed on a graphical user interface associated with wearable computing device 110 and/or third party computing device 140. In embodiments, presentation module 128 may transmit information determined by modules 119, 160, 162, 164, 166, 168, or 169, which may be translated to be presented on a display or user interface. For example, data transmitted by presentation module 128 may be configured to indicate a heart rate, blood oxygen level, body temperature, etc., of a wearer of wearable computing device 110 to a third party computing device 140. Accordingly, a third party associated with third party computing device 140 may confirm an emergency alert signal transmitted by alert module 178, or further monitor information determined by wearable computing device 110.

Third computing device 140 may be a smart phone, tablet computer, laptop computer, wearable computer, personal data assistant, desktop computer, or any other type of device with a hardware processor that is configured to process instructions and connect to network 130, one or more portions of network 130, biometric server 120 and/or wearable computing device 110. Third party computing device 140 may include processing device 142, communication device 144, a memory device 146, and a user interface 148.

Processing device 142 can include memory, e.g., read only memory (ROM) and random access memory (RAM), storing processor-executable instructions and one or more processors that execute the processor-executable instructions. In embodiments where processing device 142 includes two or more processors, the processors may operate in a parallel or a distributed manner. Processing device 142 may execute an operating system of venue computing device 140 or software associated with other elements of client computing device 140.

Communication device 144 may be a device that allows venue computing device 144 to communicate with another device, e.g., biometric server 120 over network 130. Communication device 144 may include one or more wireless transceivers for performing wireless communication and/or one or more communication ports for performing wired communication.

Memory device 146 may be a device configured to store data generated or received by third party computing device 140. Memory device 146 may include, but is not limited to a hard disc drive, an optical disc drive, and/or a flash memory drive. Memory device 146 may be configured to store data determined by wearable computing device 110 or biometric server 120.

User interface 148 may be a device that allows a third party to interact with third party computing device 140 or biometric server 110 over network 130. While one user interface is shown, the term "user interface" may include, but is not limited to being, a touch screen, a physical keyboard, a mouse, a camera, a video camera, a microphone, vibrating motor, haptic device, and/or a speaker. Utilizing user interface 148, a third party may be presented with information associated with an alert signal from biometric server 120. The information associated with the alert signal may be biographic information of the user of wearable technology, the location of the emergency situation, the type of emergency situation, the time the emergency situation is detected, etc.

One skilled in the art will appreciate that the above modules, devices, processors, etc. depicted in topology 100 may be present in a plurality of elements. For example, in other embodiments wearable computing device 110 may be configured to transmit an alert signal to a third party computing device 140, independent of biometric server 120. Further, the modules depicted in wearable computing device 110, biometric server 120, and/or third party computing device 140 may disposed in other elements within the topology 100. For example, in an embodiment, wearable computing device 110 may include an alert module 178 and/or a presentation module 128.

Figure 2:
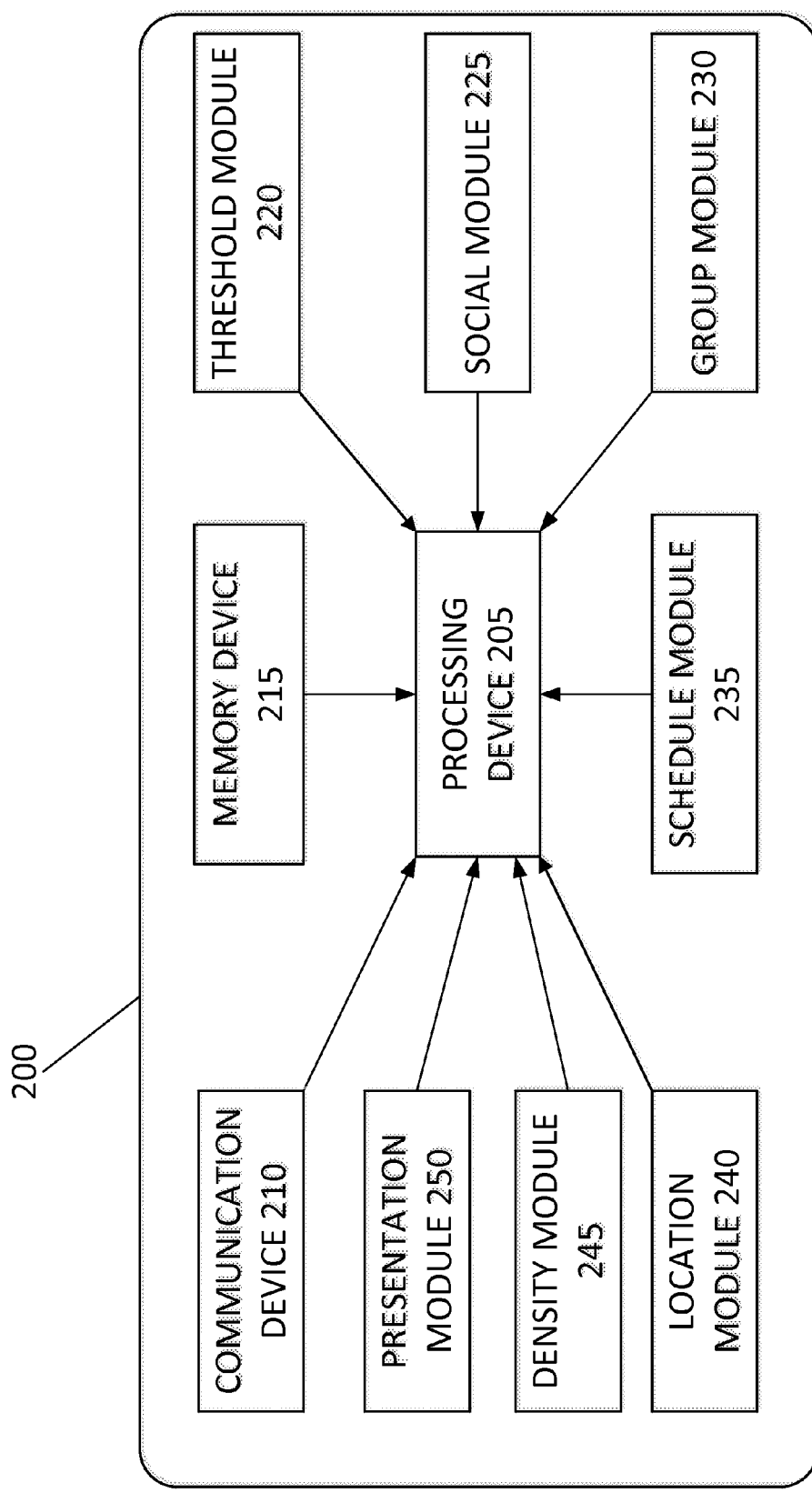
FIG. 2 depicts one embodiment of a biometric server.

FIG. 2 depicts one embodiment of biometric server 200. Biometric server 120 may include a processing device 205, communication device 210, memory device 215, threshold module 220, social module 225, group module 230, schedule module 235, location module 240, density module 245, and presentation module 250. One skilled in the art will appreciate that modules and/or devices described in FIG. 2 may work along with biometric server 120 described in FIG. 1. Additionally, for the sake of brevity a description of certain modules presented in FIG. 2 are omitted.

Threshold module 220 may be a hardware computing device configured to set the threshold ranges and/or change thresholds associated with a wearer of wearable computing device 110. The threshold ranges may have an upper bound and/or a lower bound that are associated with a user's biometric data. In embodiments, the threshold ranges may have first upper bound and a second upper bound, and a first lower bound and a second lower bound, wherein the first upper bound and lower bound may be within the second upper bound and second lower bound. Utilizing the first upper and lower bounds and the second upper and lower bounds, a wearer may adjust the threshold ranges for situations where a user is performing physical activity versus an emergency situation.

Social module 225 may be a hardware processing device configured to allow the wearer of wearable computing device 110 to generate and create a user profile on a social network. Social module 225 may also be configured to allow the wearer to establish links between users based on relationships with users within online communities.

Group module 230 may be a hardware processing device configured to allow the wearer of wearable computing device 110 to establishment groups of users on the online community. The groups of users may be based on different associations that the wearer may take part in. For example, a first group may be associated with work colleagues of the wearer, a second group may be associated with school colleagues of the wearer, a third group may be associated with teammates of the wearer on a sports team, etc. Accordingly, different groups may be formed on the online community, wherein the groups may be associated with the same or different individuals. In embodiments, the groups may be utilized to delineate third parties or individuals that may receive emergency alert signals. A group may be initiated by a single communication (e.g., a request) initiated by the wearer requesting a group be formed between the wearer and one or more other users. Subsequently, other users may be added to the group via requests from the wearer. In embodiments, the wearer may transmit requests to other users, such as friends on the online community, and to let the other users join the group.

Schedule module 235 may be a hardware processing device configured to determine schedules associated with different groups. The schedule may include time periods throughout a day, week, month, year, etc. The different time periods may correspond with when users within groups should receive an emergency alert signal for the wearer of wearable computing device 110. Responsive to an alert module determining an emergency alert signal should be transmitted, schedule module 235 may transmit the emergency alert signal to users within the group(s) with schedules corresponding to the current date and time. For example, a first group may be associated with a work group with time periods corresponding to 9 AM to 5 PM Monday through Friday, and a second group may be associated with a sports group with time periods corresponding to 7 PM to 9 PM Tuesdays and Saturdays. If an alert module determines that an emergency alert signal should be transmitted at 4 PM on a Wednesday, schedule module 235 may determine groups that the wearer is associated with at the current time, and transmit the emergency alert signal to the users within the corresponding groups.

Density module 245 may be a hardware processing device configured to determine the number of users of wearable computing devices within a given geographic region transmitting emergency alert signals over a time period. Responsive to transmitting an emergency alert signal associated with wearable computing device 110, density module 245 may determine a geographic region associated with wearable computing device 110 based on the location of wearable computing device. The geographic region may be based on a radius surrounding wearable computing device 110, a zip code associated with the current location of wearable computing device 110, etc. Density module 245 may then determine an aggregate number of wearable computing devices associated with transmitted emergency alert signals within the geographic region over a period of time (e.g. 1 second, ten seconds, one minute, ten minutes, one hour, etc.) after the emergency alert signal associated with wearable computing device 110 is transmitted. If the aggregate number for the given region is greater than a density threshold, then density module 245 may transmit a notification signal to users within a wearer's social network or located within a close proximity to the given region. The notification signal may include information corresponding to the geographic area (e.g. zip code, cross streets, map data, etc.) and the aggregate number.

In embodiments, responsive to the aggregate number of wearable computing devices no longer being associated with emergency alert signals falls below the aggregate threshold, a second notification signal may be transmitted. The second notification may be transmitted after a given period of time (e.g. every 5 minutes, one hour, etc.) after determining that the aggregate number of wearable computing devices is no longer associated with an emergency alert signal.

Figure 3:
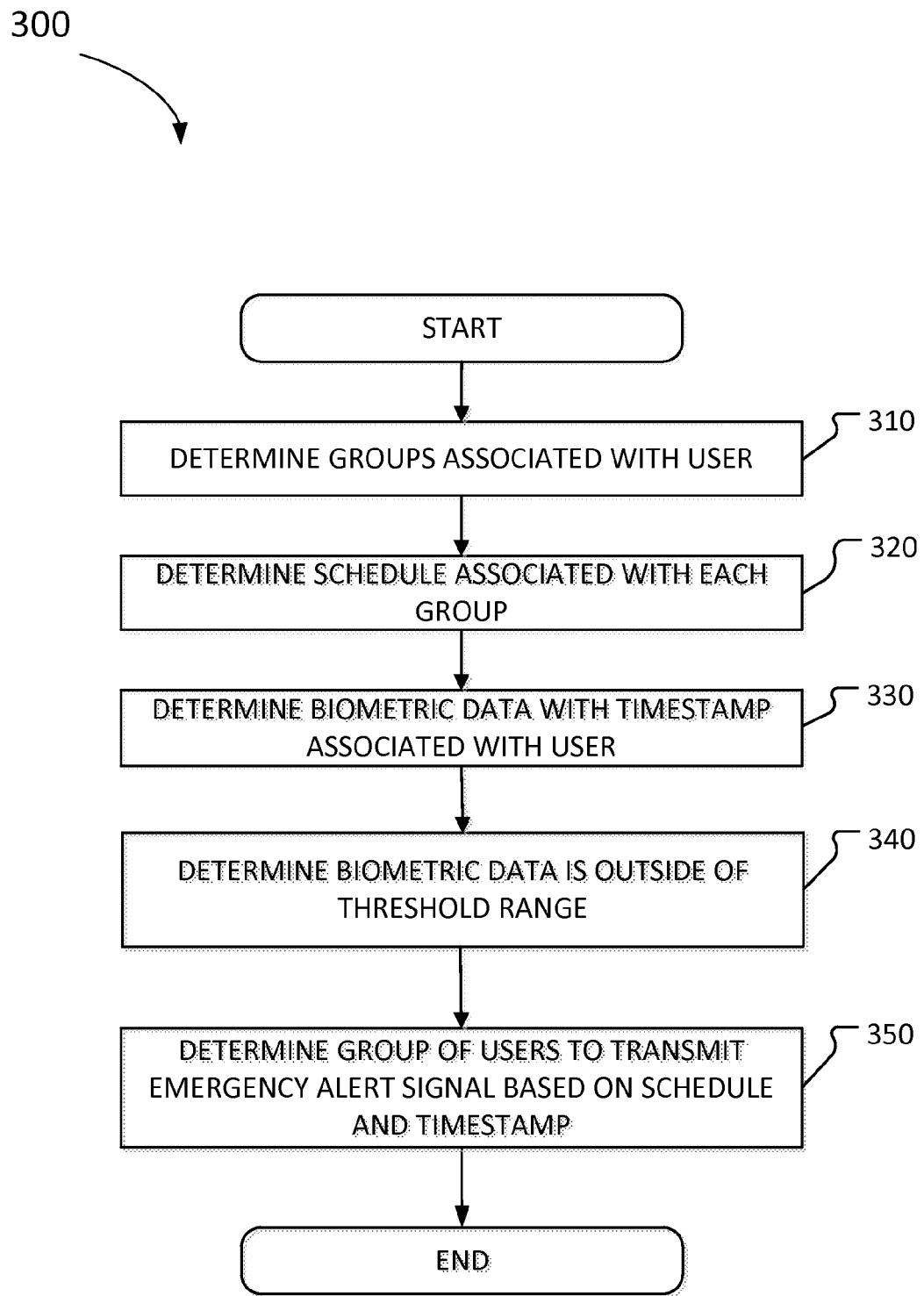
FIG. 3 depicts one embodiment of a method for transmitting emergency alert signals.

FIG. 3 illustrates a method 300 for transmitting emergency alert signals. The operations of method 300 presented below are intended to be illustrative. In some embodiments, method 300 may be accomplished with one or more additional operations not described, and/or without one or more of the operations discussed. Additionally, the order in which the operations of method 300 are illustrated in FIG. 3 and described below is not intended to be limiting.

In some embodiments, method 300 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 300 in response to instructions stored electronically on an electronic storage medium. The one or more processing devices may include one or more devices configured through hardware, firmware, and/or software to be specifically designed for execution of one or more of the operations of method 300.

At operation 310, groups associated with a user of a wearable computing device may be determined. The groups may be associated with affiliations, activities, hobbies, work, etc. that the user is associated with. The groups may include other users that are within the groups. For example, a first group may be associated with co-workers of the user, a second group may include family of the user, a third group may include teammates of the user, etc. Operation 310 may be performed by a group module that is the same as or similar to group module 230, in accordance with one or more implementation.

At operation 320, schedules associated with the different groups may be determined. The schedules may be associated with a time period that the user will take part in group activities. For example, time periods associated with the first group may be 9 AM to 5 PM Mondays through Fridays, time periods associated with the second group may be all the time, and time periods associated with the third group may be 7 PM to 9 PM Tuesdays and Fridays. Operation 320 may be performed by a schedule module that is the same as or similar to schedule module 235, in accordance with one or more implementation. At operation 330, biometric data associated with the user and a timestamp associated with the biometric data may be received. The biometric data may include a heart rate for the user, blood alcohol level of the user, etc. Operation 330 may be performed by a profile module that is the same as or similar to profile module 170, in accordance with one or more implementation.

At operation 340, it may be determined that the received biometric data is outside of a range threshold. Responsive to determining the biometric data is outside of a range threshold, it may be determined that an emergency alert signal should be transmitted. Operation 340 may be performed by an alert module that is the same as or similar to alert module 178, in accordance with one or more implementation.

At operation 350, the emergency alert signal may be transmitted to users within a group, wherein the group may be determined based on the timestamp and the user's schedule. Responsive to determining an emergency alert signal should be transmitted, groups that the user is part of having a schedule associated with the time of day corresponding to the timestamp may be determined. Furthermore, the emergency alert signal may be transmitted to the users within the group(s) with a schedule corresponding to the timestamp. Operation 350 may be performed by an alert module that is the same as or similar to alert module 178, in accordance with one or more implementation.

Figure 4:
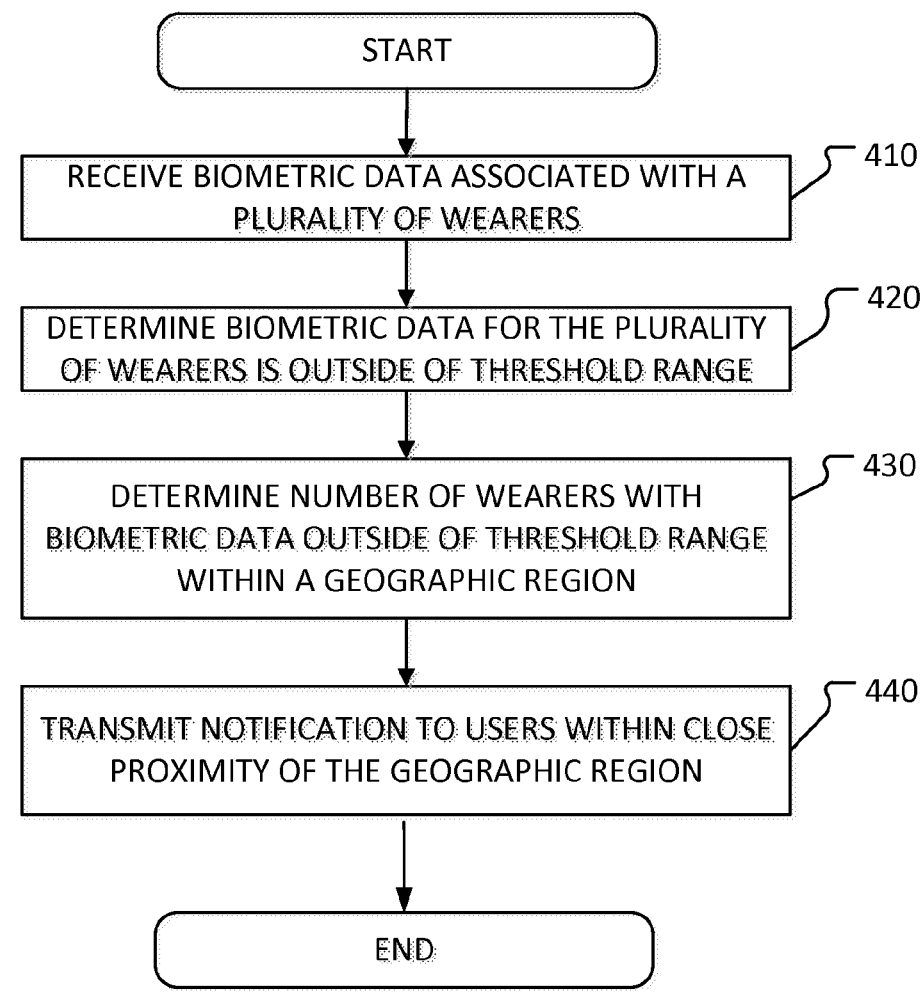
FIG. 4 depicts one embodiments of a method for transmitting emergency alert signals.

FIG. 4 illustrates a method 400 for transmitting emergency alert signals. The operations of method 400 presented below are intended to be illustrative. In some embodiments, method 400 may be accomplished with one or more additional operations not described, and/or without one or more of the operations discussed. Additionally, the order in which the operations of method 400 are illustrated in FIG. 4 and described below is not intended to be limiting.

In some embodiments, method 400 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 400 in response to instructions stored electronically on an electronic storage medium. The one or more processing devices may include one or more devices configured through hardware, firmware, and/or software to be specifically designed for execution of one or more of the operations of method 400.

At operation 410, biometric data associated with wearers of a plurality of wearable computing devices may be determined along with location data corresponding to each of the corresponding wearable computing devices. The biometric data may include a heart rate for the user, blood alcohol level of the user, etc. Operation 430 may be performed by a profile module that is the same as or similar to profile module 170, in accordance with one or more implementation.

At operation 420, it may be determined that the received biometric data associated with the plurality of the wearable computing devices within a geographic region at operation 410 is outside of a range threshold. Operation 420 may be performed by an alert module that is the same as or similar to alert module 178, in accordance with one or more implementation.

At operation 430, the number of wearable computing devices indicating that a corresponding user within the given geographic region has biometric data being outside of the range threshold may be determined. Operation 430 may be performed by a density module that is the same as or similar to density module 245, in accordance with one or more implementation.

At operation 440, a notification may be transmitted to users that are in close proximity (e.g. one mile, two miles, etc.) to the geographic region. In embodiments, the proximity of the other users may be determined based on the distance from the current location of the user to the geographic region. The notification may include a warning that users within the geographic region have transmitted an emergency alert signal, the location of the geographic region, and the type of emergency alert signal that was transmitted. Operation 440 may be performed by a presentation module that is the same as or similar to presentation module 178, in accordance with one or more implementation.

Although the present technology has been described in detail for the purpose of illustration based on what is currently considered to be the most practical and preferred implementations, it is to be understood that such detail is solely for that purpose and that the technology is not limited to the disclosed implementations, but, on the contrary, is intended to cover modifications and equivalent arrangements that are within the spirit and scope of the appended claims. For example, it is to be understood that the present technology contemplates that, to the extent possible, one or more features of any implementation can be combined with one or more features of any other implementation.

Reference throughout this specification to "one embodiment", "an embodiment", "one example" or "an example" means that a particular feature, structure or characteristic described in connection with the embodiment or example is included in at least one embodiment of the present invention. Thus, appearances of the phrases "in one embodiment", "in an embodiment", "one example" or "an example" in various places throughout this specification are not necessarily all referring to the same embodiment or example. Furthermore, the particular features, structures or characteristics may be combined in any suitable combinations and/or sub-combinations in one or more embodiments or examples. In addition, it is appreciated that the figures provided herewith are for explanation purposes to persons ordinarily skilled in the art and that the drawings are not necessarily drawn to scale.

Embodiments in accordance with the present invention may be embodied as an apparatus, method, or computer program product. Accordingly, the present embodiments may take the form of an entirely hardware embodiment, an entirely software embodiment (including firmware, resident software, micro-code, etc.), or an embodiment combining software and hardware aspects that may all generally be referred to herein as a "module" or "system." Furthermore, the present invention may take the form of a computer program product embodied in any tangible medium of expression having computer-usable program code embodied in the medium.

Any combination of one or more computer-usable or computer-readable media may be utilized. For example, a computer-readable medium may include one or more of a portable computer diskette, a hard disk, a random access memory (RAM) device, a read-only memory (ROM) device, an erasable programmable read-only memory (EPROM or Flash memory) device, a portable compact disc read-only memory (CDROM), an optical storage device, and a magnetic storage device. Computer program code for carrying out operations of the present invention may be written in any combination of one or more programming languages.

The flowcharts and block diagrams in the flow diagrams illustrate the architecture, functionality, and operation of possible implementations of systems, methods, and computer program products according to various embodiments of the present invention. In this regard, each block in the flowcharts or block diagrams may represent a module, segment, or portion of code, which comprises one or more executable instructions for implementing the specified logical function(s). It will also be noted that each block of the block diagrams and/or flowchart illustrations, and combinations of blocks in the block diagrams and/or flowchart illustrations, may be implemented by special purpose hardware-based systems that perform the specified functions or acts, or combinations of special purpose hardware and computer instructions. These computer program instructions may also be stored in a computer-readable medium that can direct a computer or other programmable data processing apparatus to function in a particular manner, such that the instructions stored in the computer-readable medium produce an article of manufacture including instruction means which implement the function/act specified in the flowcharts and/or block diagrams.

What is claimed is:

1. A notification system comprising:
    a profile module configured to receive biometric data from a wearable computing device over a network, wherein the biometric data is associated with a wearer of the wearable computing device;
    a threshold module configured to determine that the received biometric data is outside of a threshold range;
    a group module configured to determine at least one user within a first group, the first group having a first set of wearable computing devices, the first group including the at least one user associated with the wearer on the wearable computing device on a social network and, wherein the profile module is configured to receive biometric data from first set of wearable computing devices;
    an alert module configured to transmit an emergency alert signal to the user within the group responsive to determining that the received biometric data is outside of the threshold range;
    a location module configured to determine the locations associated with each of the first set of wearable computing devices and a second set of wearable computing devices, the locations associated with second set of wearable computing device being within a predetermined distance from a geographic region, the geographic region having a first size, the predetermined distance from the geographic region having a second size, the second size being greater than the first size;
    a density module configured to determine an aggregate number of the first set of wearable computing devices having received biometric data is outside of the threshold range within the geographic region, wherein the alert module is configured to transmit a notification signal to the second set of wearable computing devices responsive to determining that the aggregate number of the first set of wearable computing devices having received biometric data is outside of the threshold range within the geographic region.

2. The system of claim 1, wherein the biometric data includes at least one of heart monitor data, skin monitor data, and blood alcohol level data.

3. The system of claim 1, further comprising:
    a schedule module configured to determine a schedule corresponding to the first group, the schedule including a time period and a day of the week.

4. The system of claim 3, wherein the biometric data includes a timestamp, and the schedule module is configured to determine that the timestamp corresponds to the schedule of the first group.

5. The system of claim 4, wherein the first group includes a plurality of users, and the alert module is configured to transmit the emergency alert signal to each of the plurality of users within the first group.

6. The system of claim 3, wherein the group module is configured to determine a plurality of groups associated with the wearer of the wearable computing device, each of the groups having a different schedule.

7. The system of claim 6, wherein the alert module is configured to transmit the emergency alert signal only to users within the groups having schedules corresponding to the timestamp.

* * * * *